US 11,725,175 B2

(12) United States Patent
Shkolnikov et al.

(10) Patent No.: US 11,725,175 B2
(45) Date of Patent: Aug. 15, 2023

(54) ELECTROPORATION

(71) Applicant: HEWLETT-PACKARD DEVELOPMENT COMPANY, L.P., Spring, TX (US)

(72) Inventors: Viktor Shkolnikov, Palo Alto, CA (US); Diane R. Hammerstad, Corvallis, OR (US); Michael W. Cumbie, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 130 days.

(21) Appl. No.: 16/605,193

(22) PCT Filed: Sep. 23, 2017

(86) PCT No.: PCT/US2017/053121
§ 371 (c)(1),
(2) Date: Oct. 14, 2019

(87) PCT Pub. No.: WO2019/059936
PCT Pub. Date: Mar. 28, 2019

(65) Prior Publication Data
US 2020/0224145 A1 Jul. 16, 2020

(51) Int. Cl.
*C12M 1/42* (2006.01)
*C12M 1/26* (2006.01)
(Continued)

(52) U.S. Cl.
CPC .............. *C12M 35/02* (2013.01); *C12M 1/42* (2013.01); *C12M 3/006* (2013.01); *C12M 33/04* (2013.01);
(Continued)

(58) Field of Classification Search
None
See application file for complete search history.

(56) References Cited

U.S. PATENT DOCUMENTS 5,230,026 A * 7/1993 Ohta ...................... G06V 10/28
382/273
6,824,974 B2 11/2004 Pisharody et al.
(Continued)

FOREIGN PATENT DOCUMENTS

RU 2488629 C1 7/2013
WO WO2003049806 A1 6/2003
(Continued)

OTHER PUBLICATIONS

Nishiyama et al., "Development of a Three-Dimensional Bioprinter: Construction of Cell Supporting Structures Using Hydrogel and State-of-the-Art Inkjet", Journal of Biomechanical Engineering, Mar. 2009, vol. 131 / 035001-1-035001-6. (Year: 2009).*
(Continued)

*Primary Examiner* — William H. Beisner
(74) *Attorney, Agent, or Firm* — Foley & Lardner LLP

(57) ABSTRACT

An electroporation system may include a well plate, a dispenser and a dispenser-well positioning system. The well plate may include wells, each of the wells including an interior, a first electrode adjacent the interior and a second electrode adjacent the interior and spaced from the first electrode. The first electrode and the second electrode are to apply an electrostatic field across the well. The dispenser is to dispense a cell having a diameter into each of the wells. The dispenser-well positioning system is to align each well and the dispenser such that the dispenser dispenses the cell into each well at a location spaced from the first electrode and the second electrode by a distance of at least 5 times the diameter of the cell.

18 Claims, 4 Drawing Sheets

(51) Int. Cl.
- *C12M 1/36* (2006.01)
- *C12N 13/00* (2006.01)
- *C12N 15/87* (2006.01)
- *C12M 3/00* (2006.01)
- *A61N 1/10* (2006.01)
- *C12M 1/00* (2006.01)

(52) U.S. Cl.
CPC ............. *C12M 41/48* (2013.01); *C12N 13/00* (2013.01); *C12N 15/87* (2013.01); *A61N 1/10* (2013.01); *C12M 45/07* (2013.01)

(56) References Cited

U.S. PATENT DOCUMENTS

| | | | |
|---|---|---|---|
| 7,276,206 B2 | 10/2007 | Augustine et al. | |
| 8,222,014 B2 | 7/2012 | Firth et al. | |
| 8,232,074 B2 | 7/2012 | Jardemark et al. | |
| 2001/0005489 A1* | 6/2001 | Roach | B01L 13/02 204/600 |
| 2002/0094578 A1* | 7/2002 | Kowallis | B01L 3/5085 422/63 |
| 2006/0115888 A1* | 6/2006 | Gamelin | C12M 41/48 435/305.1 |
| 2008/0070311 A1 | 3/2008 | Li | |
| 2009/0053813 A1 | 2/2009 | Evans | |
| 2012/0194664 A1* | 8/2012 | Kiyota | C12M 41/48 348/79 |
| 2016/0102282 A1* | 4/2016 | Choi | C12M 35/02 435/289.1 |

FOREIGN PATENT DOCUMENTS

| | | |
|---|---|---|
| WO | WO2004050866 A1 | 6/2004 |
| WO | WO2011127040 A2 | 10/2011 |

OTHER PUBLICATIONS

Pepper et al. "Design and Implementation of a Two-Dimensional Inkjet Bioprinter," 31st Annual International Conference of the IEEE EMBS Minneapolis, Minnesota, USA, Sep. 2-6, 2009, pp. 6001-6005. (Year: 2009).*

Yusof et al., "Inkjet-like printing of single-cells," Lab Chip, 2011, 11, 2447-2454. (Year: 2011).*

Potter, H. et al., "Transfection by Electroporation", 2018, Current Protocols in Molecular Biology, 121(1).

* cited by examiner

ELECTROPORATION

BACKGROUND

Electroporation is a microbiology technique in which an electric field is applied to cells to increase the permeability of the cell membrane, facilitating the introduction of an agent, such as a nucleic acid, into the cells through transfection. The transfection of cells with at least one agent may have many applications in biology and medicine. For example, transfection may be utilized to insert DNA into a cell along with proteins that incorporate the DNA into the cell's genome. Incorporation of the DNA into the cell's genome may be utilized to create genetically modified organisms.

Figure 1:
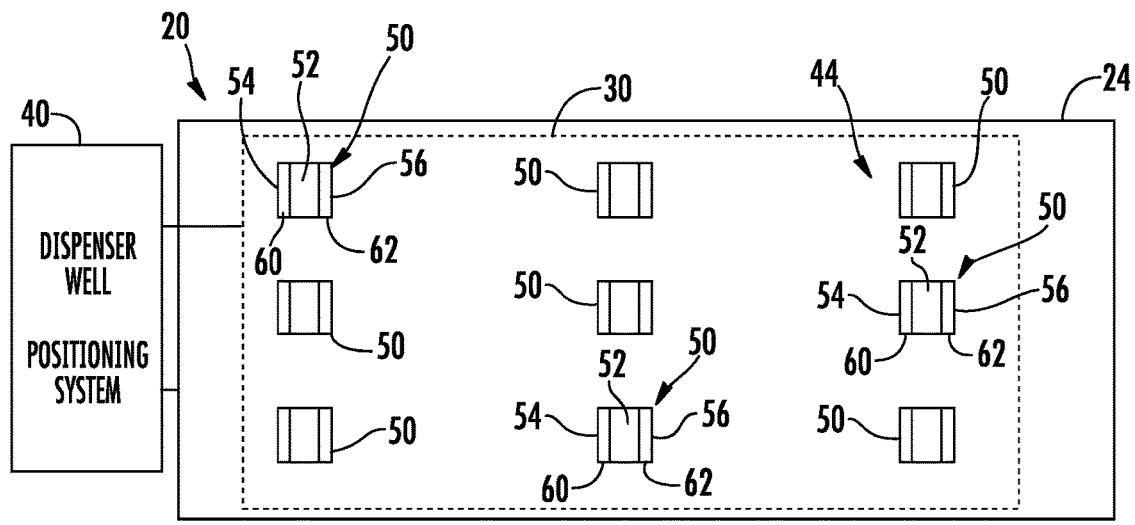
FIG. 1 is a top view schematically illustrating portions of an example electroporation system.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION OF EXAMPLES

Existing electroporation processes are often labor-intensive and time-consuming. Many such electroporation processes (also referred to as electro transfection processes) involve manual placement of cells into a transfection chamber and removal of the cells, one batch at a time. Many such electroporation processes may not effectively deliver transfection agents, such as nucleic acids or plasmids, into the cell.

Moreover, such existing electroporation processes often inefficiently utilize the available cells. In some applications, there is a limited supply of the cells that are to undergo electroporation. It has been discovered that in many electroporation processes, the cells often become damaged. It has further been discovered that such damage to the cells may be reduced or avoided by precisely locating the cells at controlled locations between and spaced from the electrodes that create the electric field during electroporation.

Disclosed herein are example electroporation systems and methods that facilitate economical and efficient automated electroporation of cells. Disclosed herein are example electroporation systems and methods that comprise a dispenser-well positioning system that provides controlled positioning or dispensing of cells into electroporation wells at precise locations spaced from the electrostatic field generating electrodes to reduce damage to the cells during electroporation.

Disclosed herein are example electroporation systems and methods that provide automated concurrent electroporation/transfection of different cell types, with different transfection agents, with different electroporation solutions and with different electrical conditions or electrostatic fields in different wells of a well plate. Disclosed herein are example electroporation systems and methods that facilitate the automated identification of values for electrostatic fields that enhance electroporation of the cells. Such automation facilitates high transfection efficiency and reproducible transfection efficiency.

Disclosed herein is an example electroporation system that may comprise a well plate, a dispenser and a dispenser-well positioning system. The well plate may include wells. Each well may include an interior, a first electrode adjacent the interior and a second electrode adjacent the interior and spaced from the first electrode. The first electrode and the second electrode are to apply an electrostatic field across the well. The dispenser is to dispense a cell having a diameter into each of the wells. The dispenser-well positioning system is to align each well and the dispenser such that the dispenser dispenses the cell into each well at a location spaced from the first electrode and the second electrode by a distance of at least 5 times the diameter of the cell. In one implementation, the total distance separating the first electrode and the second electrode is no greater than 100 um, and nominally no greater than 1 mm. In such implementations, wells 50 may have a more compact arrangement for enhanced the handling, storage and manipulation.

In some implementations, the dispenser-well positioning system comprises a well support that carries a well plate providing the wells, wherein the well support has at least one datum surface that contacts a well plate to position each of the wells of the well plate at a predetermined location. In such an implementation, an actuator may move the well support and the well plate relative to the dispenser, wherein a controller is to control the actuator based upon a position of at least one datum surface and a position of the dispenser to control positioning of the well plate relative to the dispenser. In some implementations, a sensor may be utilized to precisely locate the well plate and the dispenser relative to one another. In some implementations, a second actuator may further move the dispenser relative to the well support and the well plate. In yet other implementations, an actuator may move the dispenser relative to the well support and the well plate while the well support and the well plate remains stationary.

In some implementations, the dispenser may further count the number of cells dispensed into each of the wells to facilitate efficient and economical use of such cells. In some implementations, the dispenser may further comprise a fluid jetting dispenser to facilitate precise positioning of the cells into such wells. For example, in some implementations, the fluid jetting dispenser may comprise a thermal resistive fluid actuator to eject the cell through a nozzle.

Disclosed herein is an example electroporation system that may comprise a well plate comprising wells, wherein each of the wells may include an interior, a first electrode adjacent the interior and a second electrode adjacent the interior and spaced from the first electrode. The first electrode and the second electrode cooperate to apply an electrostatic field across the well. The system may comprise reservoirs containing different types of cells and a cell dispenser. At least one actuator may be operably coupled to the well plate and the cell dispenser, wherein a controller outputs control signals: causing the at least one actuator to selectively dispense a different type of cell from the reservoirs into each of the wells; and differently charging the first electrode and the second electrode of each of the wells to form different electrostatic fields within each of the wells.

Disclosed herein is an example electroporation method which may involve dispensing cells into wells of a well plate, applying a different electrostatic field to each of the wells containing the cells, introducing a transfection agent into each of the wells, comparing an agent transfection result for each of the wells and identifying an electrostatic field for future electroporation and transfection of the agent based upon the comparison.

Figure 2:
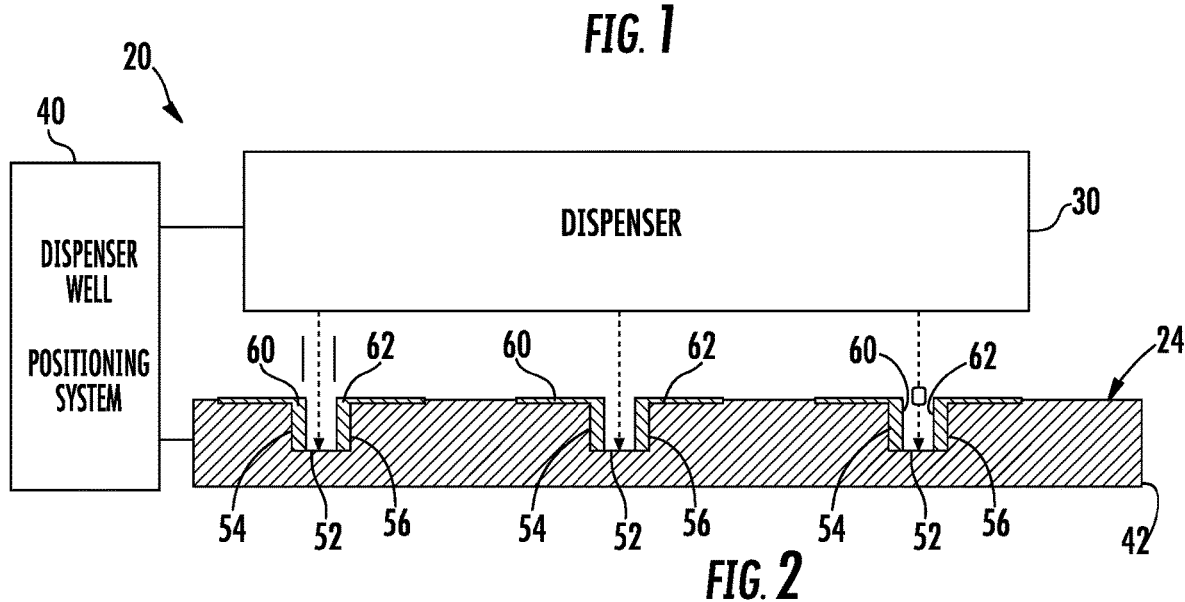
FIG. 2 is a sectional view of the example electroporation system of FIG. 1.

FIGS. 1 and 2 schematically illustrates portions of an example electroporation system 20. Electroporation system 20 facilitates the economical and efficient use of cells by reducing damage to such cells during electroporation. Electroporation system 20 reduces damage to the cells during electroporation by controllably and precisely locating or dispensing cells into each of the wells of a well plate at controlled locations that are spaced from the first and second opposing electrodes in each well. Electroporation system 20 comprises well plate 24, dispenser 30 and dispenser-well positioning system 40.

Well plate 24 comprises a structure or member 42 that provides a plurality of electroporation sites. Well plate 24 comprises an array 44 of wells 50. Each well 50 comprises a cavity extending into member 42, each cavity having a floor 52, and sidewalls 54, 56. Although each cavity is illustrated as being generally rectangular or square, in other implementations, each cavity may have other shapes. For example, in other implementations, each cavity that forms a well 50 may be cylindrical or oval in shape or may have other polygonal shapes. Although nine individual wells 50 are illustrated, arranged in a 3×3 array, well plate 24 may include any number of multiple wells which may have other patterns or arrangements.

As further shown by FIGS. 1 and 2, each of wells 50 further comprises a pair of electrodes 60, 62. Electrodes 60, 62 comprise members form from electrically conductive material, such as an electrically conductive metal, which cooperate to apply an electrostatic field across the interior of the cavity of well 50 upon being electrically charged. Electrodes 60, 62 are electrically isolated from one another, separated by floor 52, so as to form an electrical field through the contents of well 50.

In the example illustrated, electrodes 60, 62 are formed along the innermost interior side surfaces of sidewalls 54 and 56, respectively, wherein electrodes 60, 62 are directly exposed to the contents of the well 50. In such implementations, electrodes 60, 62 may extend along such sidewalls 54 and 56 and out of the well 50, along an exterior surface of member 42 for electrical connection to a charging source. Such an arrangement may facilitate fabrication of well plate 24. In other implementations, electrodes 60, 62 may be formed behind the exterior surface of walls 54 and 56, respectively, but sufficiently close to the exterior, cavity adjacent, surfaces of sidewalls 54 and 56 so as to form electric field through and across the interior of well 50.

In one implementation, each of wells 50 has a volume of between 1 ul and 1 ml. In one implementation, each of wells 50 has a depth of between 100 um and 5 cm and a cross-sectional area of between 2*10−8 m2 and 0.01 m2. In one implementation, the innermost or closest mutually facing surfaces of electrodes 60 and 62 are spaced from one another by a distance of at least 100 um and no greater than 2 cm, being nominally spaced from one another by distance of 1 mm. In other implementations, wells 50 and their electrodes 60, 62 may have other dimensions and arrangements.

In one implementation, the well plate may be molded or otherwise formed from a polymeric material, wherein a metal is evaporated or sputtered onto the polymeric plate at appropriate locations using masks so as to form electrodes 60, 62.

Dispenser 30 comprise a device connected to a source of cells to dispense a cell or multiple cells into each of the wells 50. In one implementation, dispenser 30 is positioned or is positionable over multiple wells 50 at once, wherein dispenser 30 may dispense cells into the multiple wells 50, either concurrently or at time intervals, without repositioning of dispenser 30. In one implementation, dispenser 30 is sized so as to extend opposite to each of the wells 50 of well plate 24 at the same time. In another implementation, dispenser 30 is movable, wherein dispenser-well positioning system 40 positions dispenser 30 opposite to or over each individual well 50 or groups of wells 50 that are to be provided with cells.

In one implementation, dispenser 30 comprises a fluid jetting dispenser, a dispenser that jets a stream or individual droplets of fluid containing the cell or cells being dispensed. In one implementation, dispenser 30 comprises a drop-on-demand fluid jetting device. For example, dispenser 30 may comprise a thermal resistive fluid jetting device, wherein an electrode is heated to a sufficient temper so as to vaporize adjacent fluid, creating and expanding bubble that displaces fluid and move fluid, containing a cell or cells, through a nozzle. By way of another example, dispenser 30 may comprise a membrane or diaphragm that changes shape, such as in response to an electrical charge, so as to displace adjacent fluid, containing a cell or cells, through a nozzle. In other implementations, dispenser 30 may comprise a pneumatic ejection mechanism which utilizes pressurized air or another pressurized gas to dispense fluid.

Dispenser-well positioning system 40 comprises a system to controllably position well plate 24 and dispenser 30 relative to one another to facilitate controlled dispensing of a cell or cells into each of wells 50. In one implementation, positioning system 40 comprises at least one datum surface, surface against which member 42 of well plate 24 contacts or abuts for reliable and consistent positioning of well plate 24. In one implementation, positioning system 40 may comprise at least one actuator to controllably and precisely move at least one of dispenser 30 and well plate 24 to position the outlets or nozzles of dispenser 30 at precise positions so as to dispense a cell or cells into each of wells 50 at spaced locations with respect to electrodes 60, 62 within wells 50.

For example, positioning system 40 may comprise an actuator that precisely moves dispenser 30 relative to the different wells 50. Positioning system 40 may comprise an actuator that precisely moves well plate 42 relative to the nozzles or other dispensing outlet of dispenser 30. In some implementations, positioning system 40 may move both well plate 24 and dispenser 30. In some implementations, system 40 may additionally comprise sensing devices that sense the relative positioning of well plate 24 and its wells 50 and dispenser 30, providing close loop feedback for the positioning of well plate 24 and/or dispenser 30.

Figure 3:
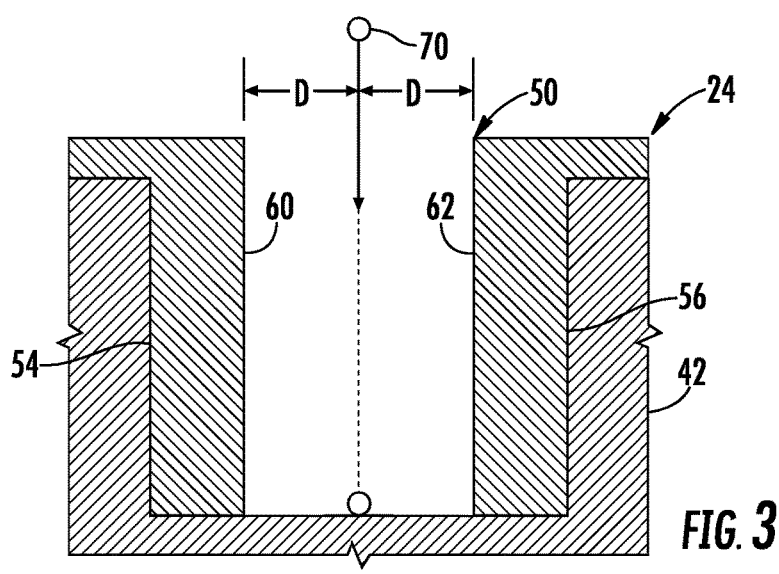
FIG. 3 is an enlarged fragmentary sectional view of an example well of the electroporation system of FIG. 1, illustrating controlled and precise depositing of a cell into the well.

FIG. 3 is an enlarged sectional view of a portion of well plate 24, illustrating the dispensing of cell 70 by dispenser 30 into an individual well 50. In the example illustrated, cell 70 has a diameter, wherein dispenser 30 (shown in FIGS. 1 and 2) directs the dispensing of cell 70 into well 50 such that cell 70 is deposited into well 50 at a location spaced from electrodes 60 and 62 by a distance D of at least five times the diameter of cell 70. In one implementation, cell 70 is deposited into well 50 at a location spaced from each of electrodes 60 and 62 by a distance D of at least 10 times the diameter of cell 70. In one implementation, cell 70 is dispensed and located within each well 50 at a center location equidistant spaced from the opposite electrodes 60 and 62. In other implementations, cell 70 may be spaced from opposite electrodes 60 and 62 by different spacings, but wherein each of the spacings is at least five times the diameter of cell 70 and, in one implementation, at least 10 times the diameter of cell 70. In some implementations, dispenser 30 may dispense multiple individual cells 70, wherein each of the individual cells 70 have the aforementioned spacing with respect to electrodes 60 and 62. In one implementation, the spacing or distance D is at least 100 um and no greater than 1 mm.

Figure 4:
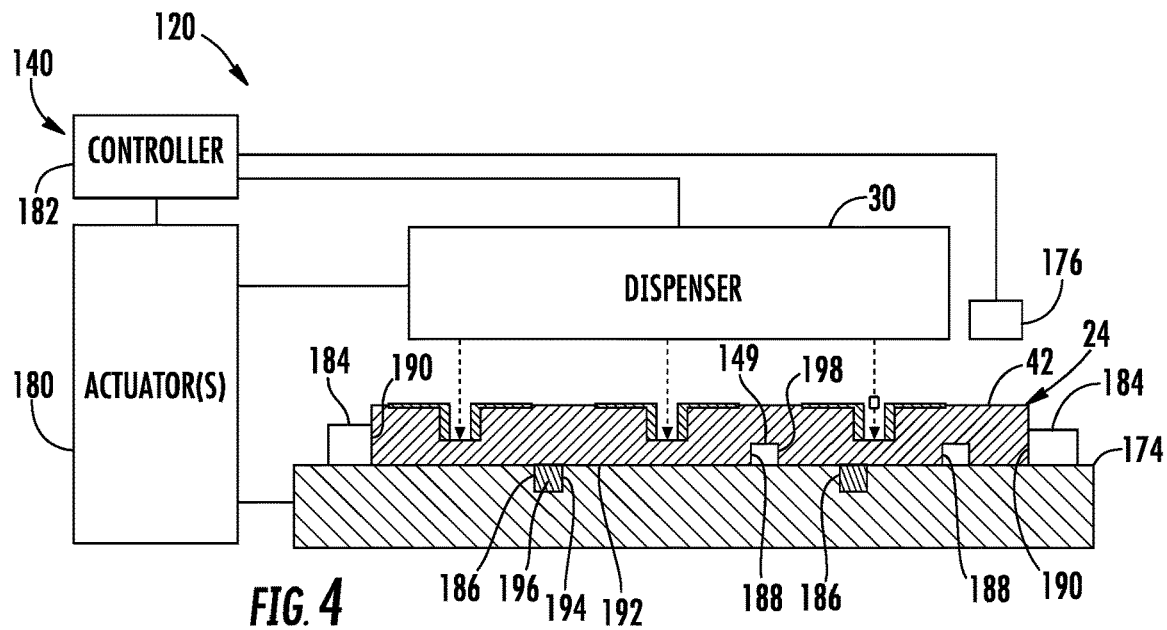
FIG. 4 is a sectional view of another example electroporation system.

FIG. 4 is a schematic diagram illustrating portions of an example electroporation system 120. Electroporation system 120 is similar to electroporation system 20 described above except that electroporation system 120 is specifically illustrated as comprising dispenser-well positioning system 140, an example of positioning system 40. Those remaining components of system 120 which correspond to components of system 20 are numbered similarly.

Positioning system 140 comprises a system to controllably positions well plate 24 and dispenser 30 relative to one another to facilitate controlled dispensing of a cell or cells into each of wells 50. Positioning system 140 comprises well support 174, sensor 176, actuators 180 and controller 182. Well support 174 comprises a structure which precisely locates well plate 24 for being aligned with dispenser 30 at predetermined relative positions. In one implementation, well support 174 is movable such that well support 134 carries well plate 24, facilitating the positioning of the various wells opposite to at least one dispensing outlet or nozzle of dispenser 30.

Well support 174 comprise at least one datum surface to contact or abut against a surface of well plate 24 to position each of the wells 50 of well plate 24 at a predetermined location. In the example illustrated, well support 174 includes various different types of datum structures which serve as reference points for locating well plate 24 and its wells 50. In the example illustrated, well support 174 comprises datum structures 184, 186 and 188. Well support 174 may include any combination of the example datum structures 184, 186 and 188.

Datum structures 184 comprise protuberances projecting along a top side of well support 174 so as to form a recess or cavity defined by datum surfaces 190 that abut opposite side faces of well plate 24. In one implementation, datum structures 184 are intermittently located about the recess or cavity that receives well plate 24. In yet another implementation, datum structures 184 may be part of a continuous ring that forms a cavity that receives well plate 24. The size and shape of the cavity formed by the continuous or spaced datum structures 184 corresponds to size and shape of well plate 24.

Datum structures 186 comprise detents that extend into a floor surface 192 upon which well plate 20 is supported or rests. The detents have interior surfaces 194 that abut the side of protuberances 196 extending from an underside of well plate 24. Datum surfaces 194 locate protuberances 196 and well plate 24 at a predetermined location relative to well support 174 to facilitate alignment of dispenser 30 with respect to the different wells 50 of well plate 24.

Datum structures 188 comprise protuberances rising above the floor surface 192 upon which well plate 20 is supported or rests. The protuberances have exterior side datum surfaces 198 that abut the sides of detents 199 that project upwardly into member 42 of well plate 24. Datum surfaces 198 locate protuberances 199 and well plate 24 at predetermined locations relative to well support 174 to facilitate alignment of dispenser 30 with respect to the different wells the of well plate 24. In some implementations, such datum surfaces may be omitted.

Sensor 176 comprises at least one sensor to sense the positioning of at least one of well plate 24 and dispenser 30. In one implementation, sensor 176 may comprise an optical sensor, such as a photo emitter-detector arrangement, to sense the positioning of either or both of well plate 24 and dispenser 30. In other implementations, sensor 176 may comprise other forms of sensing devices, such as electrical contacts or switches that sense when well plate 24 or dispenser 30 has attained a predetermined position. In some implementations, sensor 176 may be omitted.

Actuator(s) 180 comprise mechanisms that are to move at least one of well plate 24 and dispenser 30 relative to one another. In one implementation, actuator(s) 180 are operably coupled to well support 174 to move well support 174 relative to dispenser 30. In one implementation, actuator(s) 180 are operably coupled to dispenser 30 to move dispenser 30 relative to well support 174 and well plate 24. In yet another implementation, actuator(s) properly coupled to both of well support 174 and dispenser 30 to move well plate 24 and dispenser 30 relative to one another. Actuator(s) 180 have precision movement to precisely align the dispensing outlets or nozzles of dispenser 30 and wells 50 to facilitate the precise positioning of cells within wells 50 at controlled spaced locations with respect to electrodes 60, 62.

In one implementation, actuator(s) 180 may comprise two or three axis servomotors. In yet another implementation, actuators may comprise linear motors. In still other implementations, actuator(s) may comprise at least one stepper motor.

Controller 182 comprises an integrated circuit or processing unit that follows instructions contained in a non-transitory computer-readable medium so as to output control signals to control the positioning of wells 50 and dispenser 30 relative to one another and so as to control the dispensing of materials, such as cells, into such wells 50. In one implementation, controller 182 further controls the selective application of electrical charge to electrodes 60 and/or 62 so supply electric field to the deposited cells within the wells 50.

For purposes of this application, the term "processing unit" shall mean a presently developed or future developed computing hardware that executes sequences of instructions contained in a non-transitory memory. Execution of the sequences of instructions causes the processing unit to perform steps such as generating control signals. The instructions may be loaded in a non-transitory computer-readable medium such as a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 182 may be embodied as part of one or more application-specific integrated circuits (ASICs). Unless otherwise specifically noted, the controller is not limited to any specific combination of hardware circuitry and software, nor to any particular source for the instructions executed by the processing unit.

In operation, well plate 24 is positioned on well support 174, such that datum structures 184, 186 and/or 188 precisely align well plate 24 and its wells 50 respect to well support 174, the location of which is established and under the control of controller 182. Controller 182 outputs control signals which cause actuator(s) 180 to precisely position dispenser 30 and well support 174 relative to one another to align the nozzle or nozzles of dispenser 30 with respect to oppositely positioned wells 50. Such alignment may be further facilitated based upon signals received by controller 182 from sensor 176. Once alignment has been achieved, controller 182 outputs control signals causing dispenser 30 to dispense a cell or multiple cells into the aligned wells 50 such that the cell or cells are deposited into the wells 50 at spaced locations with respect to electrodes 60 and 62, providing a spacing of at least five cell diameters from the opposing electrodes 60, 62. Thereafter, the process may be repeated to dispense a cell or cells into the remaining wells 50 of well plate 24.

Upon dispensing of the cell or cells into wells 50, controller 182 may output control signals causing a source of electrical power to charge electrodes 60 and/or 62 so supply an electrostatic field across the cells to facilitate electroporation. In one implementation, each of the wells 50 of well plate 24 are first filled with a cell or cells prior to the charging of electrodes 60, 62 in the application of electric field in the wells 50. In another implementation, controller 182 may output control signals such that an electric field is applied across those wells that have received a cell or multiple cells while other cells are being dispensed in other wells of the same well plate 24.

Figure 5:
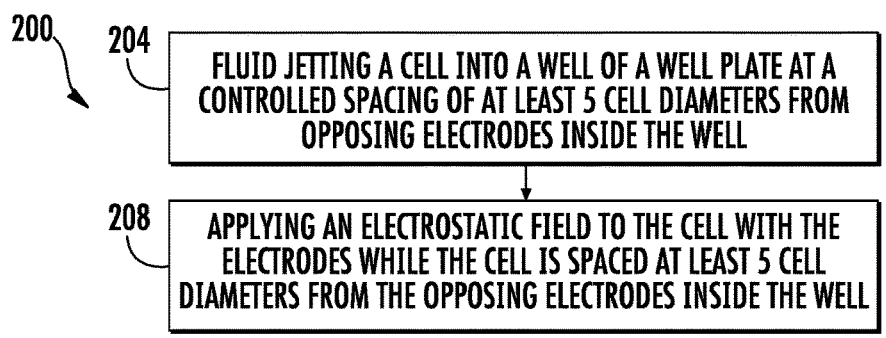
FIG. 5 is a flow diagram of an example method for electroporation.

FIG. 5 is a flow diagram of an example method 200 for performing electroporation. For ease of discussion, method 200 is described as being carried out with electroporation system 120. It should be appreciated that method 200 may be carried out with any of the electroporation system described or with other similar electroporation systems.

As indicated by block 204, fluid jetted into a well 50 of well plate 24 at a controlled spacing of at least five cell diameters from opposing electrodes 60, 62 inside the well 50. In one implementation, controller 182 outputs control signals causing actuator(s) 180 to precisely locate wells 50 of well plate 24 with respect to dispenser 30. Once the wells 50 and the dispensing nozzles of dispenser 30 have been aligned, controller 182 outputs control signals to cause fluid jetting mechanisms, such as a thermal resistive fluid jetting device, to jet a cell or cells into the well.

As indicated by block 208, controller 182 outputs control signals causing electrodes 60, 62 to apply an electrostatic field to the cell while the well is spaced at least five cell diameters from the opposing electrodes 60, 62 inside the well. In one implementation, controller 182 may supply the electrical charge to electrodes 60, 62. In another implementation, controller 182 may output control signals to an ASIC or electrical charge regulation circuitry provided on well support 174 or provided on well plate 24, causing the charge regulation circuitry, composed of electrical switches and the like, to selectively supply a regulated voltage to electrodes 60, 62. The applied electrostatic field increases the permeability of the cell membrane, facilitating the introduction of an agent, such as a nucleic acid, into the cells through transfection.

Figure 6:
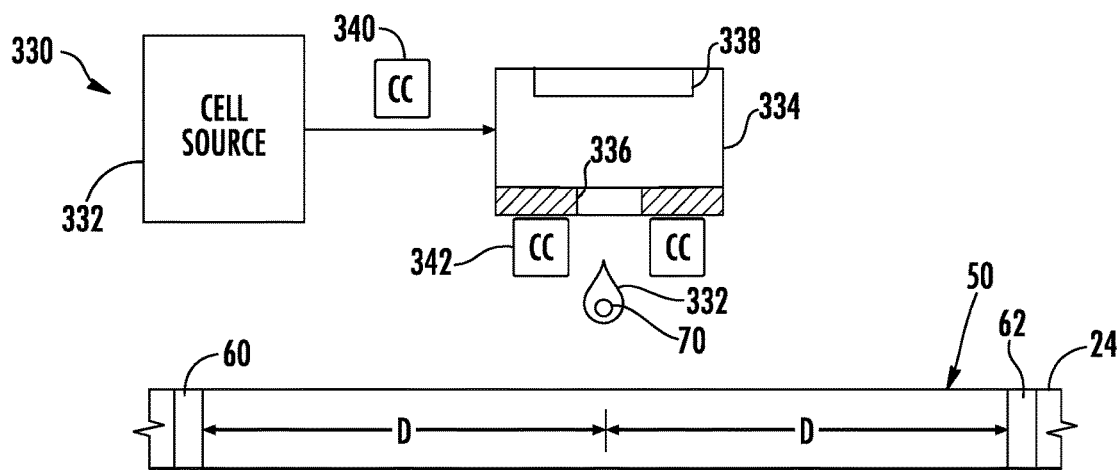
FIG. 6 is an enlarged fragmentary sectional view of an example dispenser of the example electroporation system of FIG. 1 or FIG. 4.

FIG. 6 is a schematic diagram illustrating a portion of an example dispenser 330 that may be utilized as part of electroporation systems 20 or 120. Dispenser 330 comprises a fluid jetting device that is to eject a droplet 332 of fluid containing at least one cell 70. As described above with respect to dispenser 30, dispenser 330 is controllably and precisely position relative to a well plate 24 such that the dispensed droplet 332 and its carried cell 70 are deposited and positioned within the interior of the well 50 at a spacing D of at least five cell diameters and nominally at least 10 cell diameters from electrodes 60, 62.

In the example illustrated, dispenser 330 comprises a thermal resistive fluid jetting device. Dispenser 330 comprises a cell source 332, a fluid chamber 334, and orifice are nozzle opening 336 and a thermal resistor 338. Cell source 332 comprises a port or a conduit through which the cell or cells to be deposited into well 50 are supplied into fluid chamber 334.

Fluid chamber 334 receive a cell or cells, carried in a fluid, from cell source 332 fluid chamber 334 extends adjacent to nozzle opening 336. Thermal resistor 338 resides near the opening of fluid chamber 334. Upon receiving electrical current from analytical power source, thermal resistor 338 emits heat to a sufficient extent so as to vaporize the fluid within chamber 334, creating and expanding bubble. The expanding bubble forces remaining fluid and the carried cells through nozzle opening 336 in the form of droplet 332. In other implementations, dispenser 330 may comprise other forms of controllable fluid dispensing devices.

In one implementation, dispenser 330 may additionally count the cells being dispensed in each well 50. In one implementation, cell source 332 conducts cells to fluid chamber 334, wherein the cells are counted as a travel to chamber 334. For example, in one implementation, a cell counter 340, such as an impedance sensor or an optical sensor, may be provided between cell source 332 and chamber 334. In another implementation, a cell counting sensor may be provided about or below nozzle orifice 336 to count cells as the cells are ejected through nozzle opening 336 or after such cells have been ejected through nozzle opening 336. For example, in one implementation, a cell counter 342 in the form of a photo emitter-detector sensor may optically count a number of cells ejected through nozzle opening 336. The count a number of cells may be recorded by controller 182 (shown in 4) and/or may be utilized by controller 182 two regulate the dispensing of fluid and cells by dispenser 330.

Figure 7:
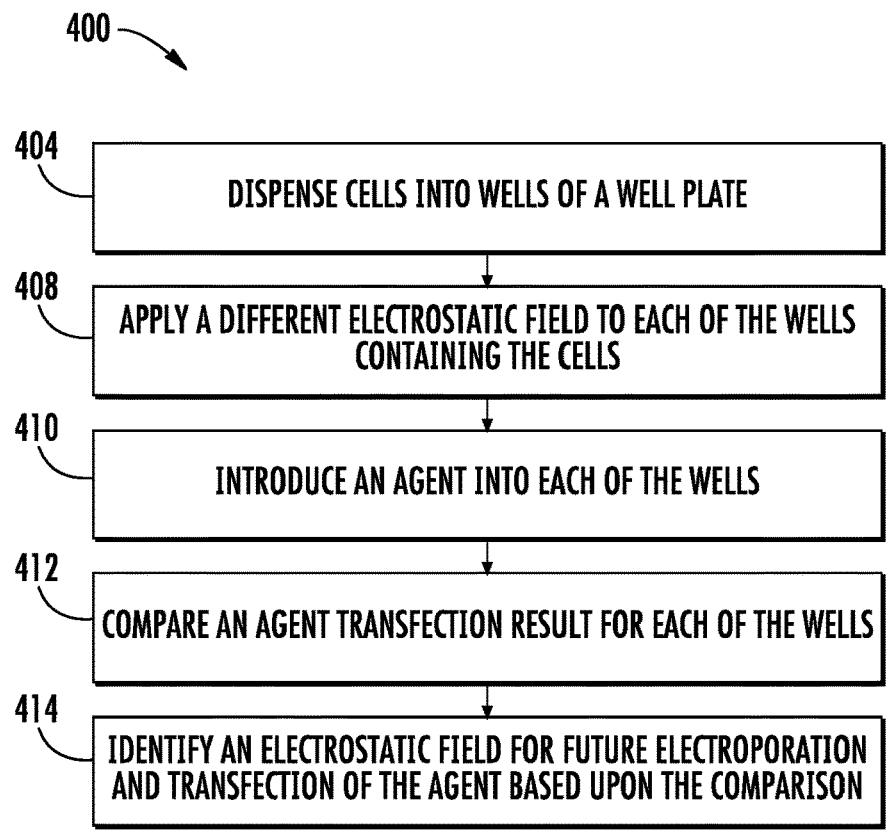
FIG. 7 is a flow diagram of an example method for identifying electrostatic fields for use in electroporation of cells.

FIG. 7 is a flow diagram of an example method 400 for identifying a value or range of values for a charge of electrostatic field that provides enhanced electroporation for a given cell type. Different values for electrostatic fields for different cells may be identified and documented, forming a library or database of electrostatic field values for different cell types and different transfection agents. In one implementation, method 400 may be carried out by system 120, wherein controller 182 outputs control signals and carries out analysis for carrying out method 400 pursuant to instructions contained in a non-transitory computer-readable medium. It should be appreciative that method 400 may be carried out with any of the disclosed systems described herein as well as other similar electroporation systems.

As indicated by block 404, cells are dispensed into wells 50 of well plate 24. In one implementation, the cells may be dispensed into wells 50 as described above, precisely depositing the cells that controlled spaced locations from the electrodes 60, 62 of wells 50. In one implementation, the cells may be positioned with a spacing of at least five cell diameters and nominally at least 10 cell diameters from electrodes 60, 62. In some implementations, the cells may be dispensed without such precise positioning in method 400.

As indicated by block 408, a different electrostatic field is applied each of the wells 50 containing the cells. For example, in one implementation, controller 182, following instructions contained in a non-transitory computer-readable medium, causes an electrical power supplier power source to differently charge electric 60, 62 of the various wells to apply the different electrostatic fields to the different wells 50. In some implementations, a first set of wells 50 may have a first electrostatic field, a second set of wells 50 may have a second electrostatic field, a third set of wells 50 may have a third electrostatic field and so on.

As indicated by block 410, a transfection agent is introduced into each of the wells 50. The transfection agent may be introduced after or prior to the application of the different electrostatic fields to the different wells 50. The transfection agent may be introduced into the cells prior to the dispensing the cells into the wells. In one implementation, dispenser 30 may additionally dispense the transfection agent into wells 50. In one implementation, dispenser 30 may dispense a transfection agent into wells 50 so as to not reposition the cells to within less than five cell diameters from the electrodes 60, 62. One example of such a transfection agent is a nucleic acid or DNA plasmid. Other examples of a transfection agent include, but are not limited to, other nucleic acids, proteins, or other molecules or particles.

As indicated by block 412, the degree of transfection for the cells is identified as compared for each of the wells. As indicated by block 414, based on the comparison, the electrostatic field that resulted in the highest transfection rate result is identified. The electrostatic field and the associated cell type and transfection agent may be catalogued or documented for future use when the particular cell type is to undergo transfection of the agent using electroporation.

Figure 8:
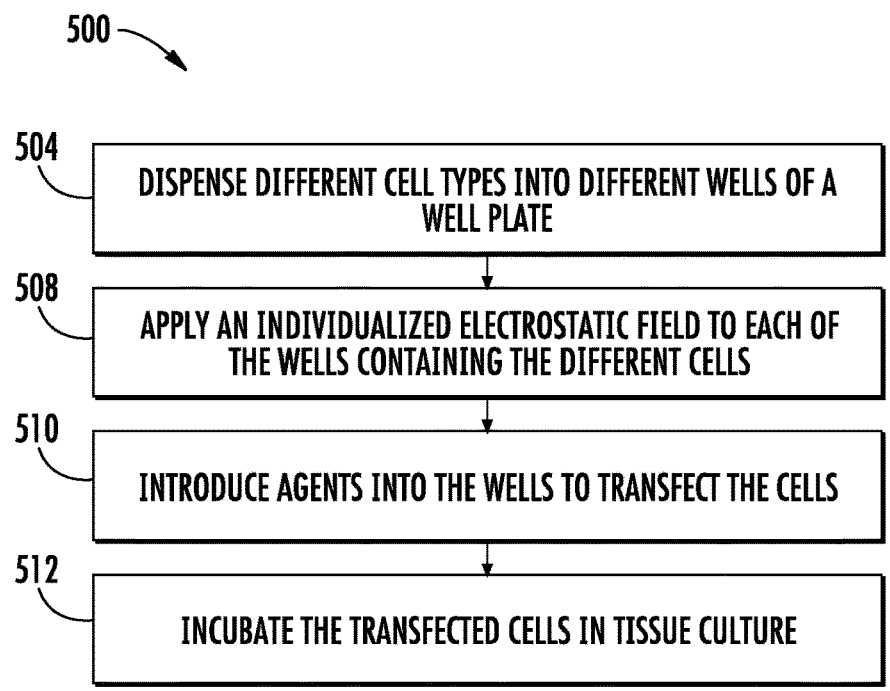
FIG. 8 is a flow diagram of an example method for the electroporation of different cell types with individualized electrostatic fields.

FIG. 8 is a flow diagram of an example method 500 for using electroporation to perform transfection on a plurality of different cell types using a single well plate. In one implementation, method 500 may be carried out by system 120, wherein controller 182 outputs control signals and carries out analysis for carrying out method 500 pursuant to instructions contained in a non-transitory computer-readable medium. It should be appreciative that method 500 may be carried out with any of the disclosed systems described herein as well as other similar electroporation systems.

As indicated by block 504, different cell types are dispensed into different wells 50 of well plate 24. In one implementation, the cells may be dispensed into wells 50 as described above, precisely depositing the cells that controlled spaced locations from the electrodes 60, 62 of wells 50. In one implementation, the cells may be positioned with a spacing of at least five cell diameters and nominally at least 10 cell diameters from electrodes 60, 62. In some implementations, the cells may be dispensed without such precise positioning in method 500.

As indicated by block 508, individualized electrostatic fields are applied to each of the wells 50 containing the cells. The individualized electrostatic fields may comprise electrostatic fields most suited for electroporation of the particular cell type in the particular well 50. For example, in one implementation, controller 182, following instructions contained in a non-transitory computer-readable medium, causes an electrical power supply or power source to differently charge electrodes 60, 62 of the various wells 50 to apply the different electrostatic fields to the different wells 50 to provide the individualized electrostatic fields for the different cell types. In some implementations, a first set of wells 50 having a first cell type may have a first electrostatic field, a second set of wells 50 having a second different cell type may have a second electrostatic field, a third set of wells 50 having a third different cell type may have a third electrostatic field and so on.

As indicated by block 510, a transfection agent is introduced into each of the wells 50. Different transfection agents, such as different DNA plasmids, may be supplied for the different cell types in the different wells 50. The transfection agent(s) may be introduced after or prior to the application of the individualized electrostatic fields to the different wells 50. The transfection agent(s) may be introduced into the cells prior to the dispensing the cells into the wells. In one implementation, dispenser 30 may additionally dispense the transfection agent(s) into wells 50. In one implementation, dispenser 30 may dispense transfection agent(s) into wells 50 so as to not reposition the cells to within less than five cell diameters from the electrodes 60, 62. One example of such a transfection agent is a nucleic acid or DNA plasmid. Other examples of a transfection agent include, but are not limited to, proteins or enzymes.

As indicated by block 512, the transfected cells are incubated in tissue culture to propagate the transfected cells. In one implementation, the transfected cells are incubated in tissue culture while remaining within their respective wells 50. In another implementation, the transfected cells are transferred to a separate incubator for incubation. The transfected cells may then be utilized or analyzed.

FIGS. 9-12 are schematic diagrams illustrating an example electroporation system 620 carrying out an example of method 500 described above. Electroporation system 620 is similar to electroporation system 120 described above except that electroporation system 620 comprises dispenser 630 in lieu of dispenser 30. Those remaining components of system 620 which correspond to components of system 120 are numbered similarly. Well support 174, actuator(s) 180, sensor 176 and actuators 180, which form part of a dispenser-well positioning system, are collectively schematically illustrated by block 140 and are described in detail respect to system 120.

Dispenser 630 is similar to dispenser 30 described above except that dispenser 630 is illustrated as specifically comprising various reservoirs 632 containing or for containing various types of cells, reservoirs 634 containing or for containing various electroporation solutions and reservoirs 636 containing or for containing various transfection agents, such as different DNA plasmids. The different reservoirs may have various arrangements or orders other than that shown. Each of reservoirs 632, 634 and 636 is associated with a corresponding fluid jetting device 638, such as the example fluid jetting device shown and described with respect to dispenser 330. Dispenser 630 may additionally comprise cell counters, such as cell counters 340 and/or 342 as described above with respect to dispenser 330.

According to one example method, controller 182 outputs control signals causing positioning system 140 to align those fluid jetting devices 638 associated with reservoir 632 with each of wells 50 or with a selected subset of wells 50. Once such alignment has been at achieved, controller 182 outputs control signals causing such fluid jetting devices 638 to deposit electroporation solutions into the wells 50. In some implementations, different electroporation solutions may be deposited into different wells 50. This process may be repeated until an electroporation solution has been deposited into each of the wells 50 of well plate 24.

Figure 9:
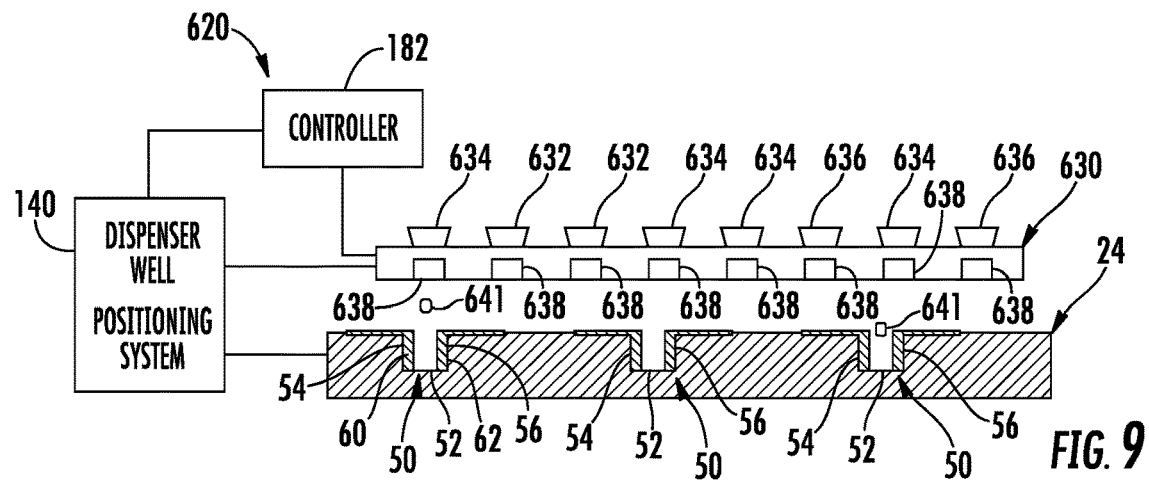
FIG. 9 is a sectional view schematically illustrating an example electroporation system during deposition of different electroporation agents into different wells of a well plate.

As shown by FIG. 9, controller 182 may output control signals causing positioning system 142 position those fluid jetting devices 638 associated with reservoirs 634 in alignment with well 50 or a selected subset of wells 50. Once such alignment has been achieved, controller 182 outputs control signals causing such fluid jetting devices 638 to deposit different transfection agents, the different DNA plasmids 641, into the aligned wells 50. This process may be repeated until each of the wells 50 of well plate 24 has received a transfection agent.

Figure 10:
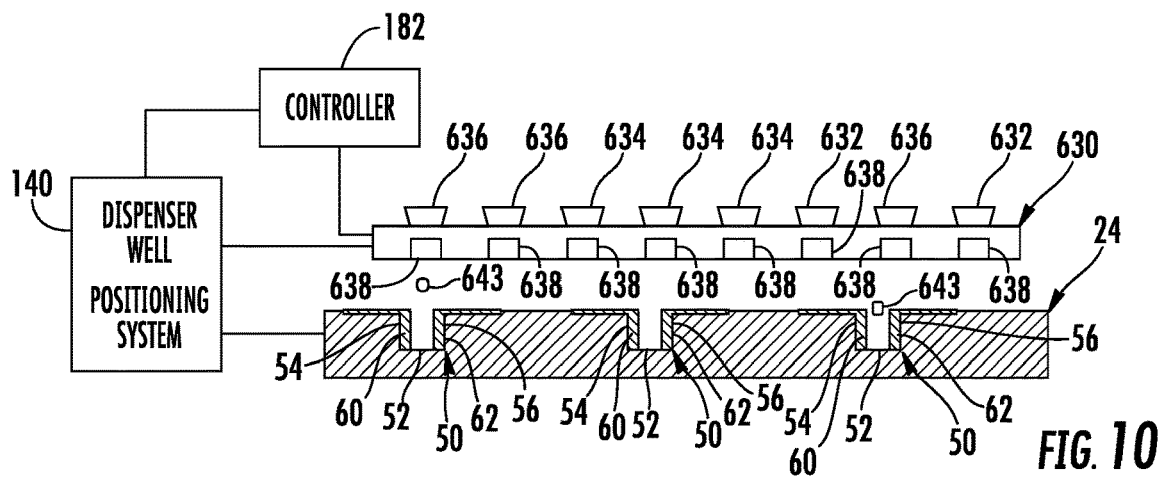
FIG. 10 is a sectional view schematically illustrating the example electroporation system of FIG. 9 during deposition of different cell types into the different wells of the well plate.

As shown by FIG. 10, controller 182 may output control signals causing positioning system 142 position those fluid jetting devices 638 associated with reservoirs 636 in alignment with wells 50 or a selected subset of wells 50. Once such alignment has been achieved, controller 182 outputs control signals causing such fluid jetting devices 638 to deposit different types of cells 643 into the aligned wells 50. This process may be repeated until each of the wells 50 of well plate 24 has received a different cell type. In some implementations, fluid jetting devices 638 may be located such that the fluid jetting devices 638 may concurrently dispense both cells and transfection agents into different cells or concurrently dispense both cells and transfection agents into the same well.

In some implementations, positioning system 140 may precisely locate and align dispenser 630 relative to the respective wells such that the different cells are deposited at a precisely controlled location within wells 50, spaced from the opposite electrodes 60, 62 by a distance of at least five cell diameters and nominally at least 10 cell diameters to reduce potential damage to such cells during electroporation, during the application of the electric field. In some implementations, the order in which the electroporation solution, the transfection agents and the different types of cells may be altered.

Figure 11:
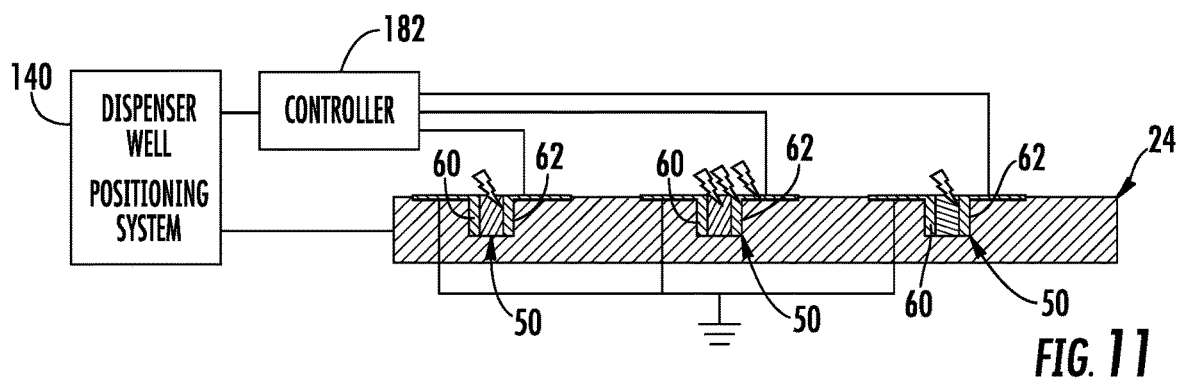
FIG. 11 is a sectional view schematically illustrating the example electroporation system of FIG. 10 during the application of individualized electrostatic fields to the different wells of the well plate that contain different electroporation solutions, different cell types and different transfection agents.

As shown by FIG. 11, controller 182 may directly supply different electrical charges or may output control signals to an electrical regulation device that causes different electrical charges to be supplied to the electrodes 60 and/or 62 of the different wells 50 so as to apply individualized electrostatic fields in the different wells 50 as described above respect to block 508 in method 500. The individualized electrostatic fields may be customized for the different wells 50 based upon the different electroporation solutions, different electroporation agents and the different cell types in the different wells 50.

Figure 12:
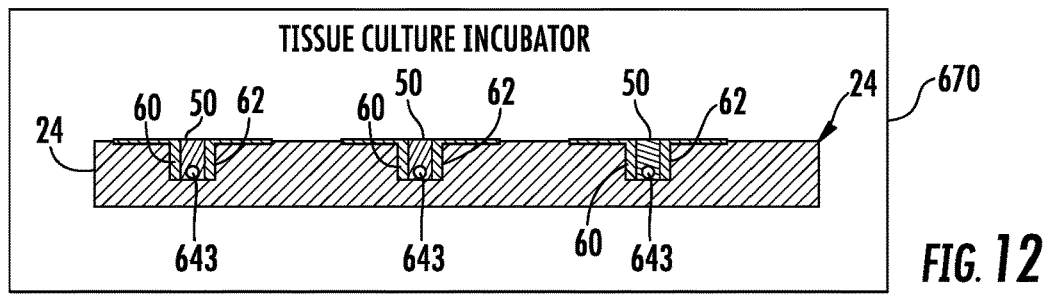
FIG. 12 is a sectional view schematically illustrating the example well plate in a tissue culture incubator to propagate the transfected cells.

As shown by FIG. 12, well plate 24 with the transfected cells 643 is stored in a tissue culture incubator 670 to allow the transfected cell 643 to propagate. As described above respect to FIGS. 9-12, system 620 facilitates the transfection of M different cell types, with N different types of transfection agents, such as different DNA plasmids, with R different electroporation solutions and with P different electrical conditions or electrostatic fields with little to no effort from a user. System 630 facilitates transfection of small amounts of fluid with small amounts of cells. The precise positioning of the cell 643 within wells 50 may allow such operations to be carried out with a fewer number of source cells due to reduced damage to such cells 643 during the application of electrostatic fields.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. An electroporation system comprising:
    a well plate comprising:
        wells, each of the wells comprising:
            an interior formed by first and second sidewalls and a floor;
            a first electrode adjacent the interior and which extends along an interior side surface of the first sidewall; and
            a second electrode adjacent the interior and which extends along an interior side surface of the second sidewall, and the second electrode being spaced from the first electrode by the floor, and the first electrode and the second electrode to apply an electrostatic field across the well;
    a well support to carry the well plate, the well support including at least one datum surface to contact the well plate to position each of the wells of the well plate;
    a dispenser including a plurality of reservoirs containing different fluids and a plurality of fluid jetting devices to selectively dispense the different fluids, including a cell having a diameter, into each of the wells; and
    a dispenser-well positioning system including a controller and actuator, wherein the controller is communicatively coupled to the actuator and programmed to align each well and the dispenser based upon a position of the at least one datum surface and a position of the dispenser such that the dispenser dispenses the cell into each well at a location spaced from the first electrode and the second electrode by a distance of at least 5 times the diameter of the cell.

2. The electroporation system of claim 1, wherein each of the first and second electrodes of the wells are directly exposed to contents of the wells, wherein the different fluids include:
fluids containing different types of cells, different types of electroporation solutions, and different types of transfection agents.

3. The electroporation system of claim 1, wherein each of the plurality of fluid jetting devices comprise a thermal resistive fluid actuator to eject the cell through a nozzle, and wherein the actuator of the dispenser-well positioning system is to move at least one of the dispenser and the well plate to position the nozzle of the dispenser at the position to dispense a cell into a respective well of the well plate at the location spaced from the first electrode and the second electrode of the respective well by the distance of at least 5 times the diameter of the cell.

4. The electroporation system of claim 1, wherein the dispenser-well positioning system comprises:
the at least one datum surface to contact the well plate to position each of the wells of the well plate at a predetermined location;
the actuator to move the well support and the well plate relative to the dispenser; and
the controller programmed to control the actuator based upon a position of the at least one datum surface and a position of the dispenser to control positioning of the well plate relative to the dispenser.

5. The electroporation system of claim 4, further comprising a second actuator to move the dispenser relative to the well support and the well plate, wherein the controller is programmed to control the second actuator based upon a position of the at least one datum surface.

6. The electroporation system of claim 1, wherein the dispenser-well positioning system comprises:
the at least one datum surface to contact the well plate to position each of the wells of the well plate at a predetermined location, the well plate includes at least one member to contact against the at least one datum surface and to position the well plate;
the actuator to move the dispenser relative to the well support and the well plate; and
the controller is programmed to control the actuator based upon a position of the at least one datum surface and the position of the dispenser to control positioning of the dispenser relative to the well plate.

7. The electroporation system of claim 1, wherein the dispenser-well positioning system comprises:
a sensor to sense the positioning of the well plate, wherein the sensor includes a photo emitter-detector arrangement or electrical contacts or switches;
the actuator operably coupled to at least one of the well plate and the dispenser to move said at least one of the well plate and the dispenser relative to one another; and
the controller is programmed to control the actuator based upon signals from the sensor indicating a sense positioning of the well plate.

8. The electroporation system of claim 1, wherein the dispenser includes at least one of an impedance sensor and an optical sensor to count a number of cells dispensed into each of the wells.

9. The electroporation system of claim 1, wherein the controller is programmed to:
differently charge the first electrode and the second electrode of each of the wells to form different P electrostatic fields within each of the wells based on cell types of cells within each of the wells;
cause the selective dispense of M different types of cells, selective dispense of N different types of transfection agents and R different electroporation solutions to the wells, and form P different electrostatic fields, wherein the different fluids include the M different types of cells, the N different types of transfection agents, and the R different electroporation solutions; and
form a library of electrostatic field values for the different types of cells and different types of transfection agents based on a comparison of an agent transfection result for each of the wells.

10. The electroporation system of claim 1, wherein the first electrode and the second electrode of each well respectively extend along the first and second sidewalls and out of each well and along an exterior surface of a member of the well plate to provide electrical connections, and the first and second electrodes are electrically isolated from one another and separated by the floor.

11. The electroporation system of claim 1, wherein the at least one datum surface is to contact the well plate to position each of the wells of the well plate at a predetermined location, the at least one datum surface including:
at least one protuberance projecting along a top side of the well support; and
at least one detent that extends into the top side of the well support; and
the controller is programmed to control the actuator to move the well support relative to the dispenser based upon the position of the at least one datum surface and the position of the dispenser to control positioning of the well plate relative to the dispenser.

12. The electroporation system of claim 1, wherein the at least one datum surface is selected from:
a protuberance projecting along a top side of the well support;
a detent that extends into the top side of the well support; and
a combination thereof, and
wherein the well plate includes at least one detent that extends into an underside of the well plate and a protuberance that extends from the underside of the well plate to abut the at least one datum surface and facilitate alignment of the dispenser with the wells of the well plate.

13. An electroporation system comprising:
a well plate comprising:
wells, each well comprising:
an interior formed by first and second sidewalls and a floor;
a first electrode adjacent the interior and which extends along an interior side surface of the first sidewall; and
a second electrode adjacent the interior and which extends along an interior side surface of the second sidewall, and the second electrode being spaced from the first electrode by the floor, and the first electrode and the second electrode to apply an electrostatic field across the well;
a well support to carry the well plate, the well support including at least one datum surface to contact the well plate to position each of the wells of the well plate;
a plurality of reservoirs containing different fluids including a plurality of different types of cells;
a cell dispenser coupled to the plurality of reservoirs and including a plurality of fluid jetting devices;

at least one actuator operably coupled to the well plate and the cell dispenser; and a controller programmed to output control signals to:
cause the at least one actuator to align each well and the cell dispenser based upon a position of the at least one datum surface and a position of the cell dispenser and to cause the cell dispenser to selectively dispense a different type of cell among the plurality of different types of cells from the plurality of reservoirs into each of the wells; and form an electrostatic field within each of the wells;

wherein the actuator and the controller form part of a dispenser-well positioning system programmed to align each well of the wells and the cell dispenser such that the cell dispenser dispenses the cell into each well at a location spaced from the first electrode and the second electrode by a distance of at least 10 times a diameter of the cell.

14. The electroporation system of claim 13, wherein the controller is programmed to differently charge the first electrode and the second electrode of each of the wells to form different electrostatic fields within each of the wells based on the different types of cells within each of the wells.

15. An electroporation system comprising:
a well plate comprising:
wells, each well comprising:
an interior formed by first and second sidewalls and a floor;
a first electrode adjacent the interior and which extends along an interior side surface of the first sidewall; and
a second electrode adjacent the interior and which extends along an interior side surface of the second sidewall, and the second electrode being spaced from the first electrode by the floor, and the first electrode and the second electrode to apply an electrostatic field across the well;
a well support to carry the well plate, the well support including at least one datum surface to contact the well plate to position each of the wells of the well plate;
a plurality of reservoirs containing different fluids including a plurality of different types of cells;
a cell dispenser coupled to the plurality of reservoirs and including a plurality of fluid jetting devices;
at least one actuator operably coupled to the well plate and the cell dispenser; and
a controller programmed to output control signals to:
cause the at least one actuator to align each well and the cell dispenser based upon a position of the at least one datum surface and a position of the cell dispenser and to cause the cell dispenser to selectively dispense a different type of cell among the plurality of different types of cells from the plurality of reservoirs into each of the wells; and
form an electrostatic field within each of the wells;
wherein the controller is programmed to:
cause selective dispense of M different types of cells, N different types of transfection agents, and R different electroporation solutions to the wells, and form P different electrostatic fields, wherein the different fluids include the M different types of cells, the N different types of transfection agents, and the R different electroporation solution.

16. An electroporation system comprising:
a well plate comprising:
wells, each well comprising:
an interior formed by first and second sidewalls and a floor;
a first electrode adjacent the interior and which extends along an interior side surface of the first sidewall; and
a second electrode adjacent the interior and which extends along an interior side surface of the second sidewall, and the second electrode being spaced from the first electrode by the floor, and the first electrode and the second electrode to apply an electrostatic field across the well;
a well support to carry the well plate, the well support including at least one datum surface to contact the well plate to position each of the wells of the well plate;
a plurality of reservoirs containing different fluids including a plurality of different types of cells;
a cell dispenser coupled to the plurality of reservoirs and including a plurality of fluid jetting devices;
at least one actuator operably coupled to the well plate and the cell dispenser; and
a controller programmed to output control signals to:
cause the at least one actuator to align each well and the cell dispenser based upon a position of the at least one datum surface and a position of the cell dispenser and to cause the cell dispenser to selectively dispense a different type of cell among the plurality of different types of cells from the plurality of reservoirs into each of the wells; and
form an electrostatic field within each of the wells;
wherein:
the first electrode and the second electrode of each the wells respectively extend along the first and second sidewalls and out of each of the wells and along an exterior surface of a member of the well plate to provide electrical connections to a charging source;
the different fluids include M different types of cells, N different types of transfection agents, and R different electroporation solutions; and
the controller is programmed to:
cause the selective dispense of the M different types of cells, selective dispense of the N different types of transfection agents and the R different electroporation solutions to the wells, and form P different electrostatic fields within the wells based on the M different types of cells;
compare an agent transfection result for each of the wells; and
identify an electrostatic field for future electroporation and transfection of a particular type of cell among the M different types of cells based upon the comparison.

17. An electroporation method to be performed in a well plate comprising wells, each well including an interior formed by first and second sidewalls and a floor, a first electrode adjacent the interior and which extends along an interior side surface of the first sidewall, and a second electrode adjacent the interior and spaced from the first electrode by the floor and which extends along an interior side surface of the second sidewall, the method comprising:
dispensing cells into wells of the well plate by a dispenser including a plurality of fluid jetting devices coupled to a plurality of reservoirs containing different fluids and a dispenser-well positioning system, including a controller, that is programmed to position the dispenser relative to the well plate based upon a position of at least one datum surface of a well support that carries the well plate and a position of the dispenser, wherein the cells are dispensed into each well at a location spaced from the first electrode and the second electrode by a distance of at least 5 times the diameter of the cell;

applying, by the first or second electrode, a different electrostatic field to each of the wells containing the cells;

introducing, by the dispenser, an agent into each of the wells;

comparing an agent transfection result for each of the wells; and identifying an electrostatic field for future electroporation and transfection of the agent based upon the comparison.

18. The method of claim 17, wherein the dispensing of the cells into the wells of the well plate comprises jetting the cells into controlled locations into each of the wells.

* * * * *